(12) United States Patent
Tian et al.

(10) Patent No.: US 12,429,699 B2
(45) Date of Patent: Sep. 30, 2025

(54) EYE MOVEMENT TRACKING DEVICE AND EYE MOVEMENT TRACKING METHOD

(71) Applicant: BOE TECHNOLOGY GROUP CO., LTD., Beijing (CN)

(72) Inventors: Wenhao Tian, Beijing (CN); Lei Wang, Beijing (CN); Xuan Feng, Beijing (CN); Yunke Qin, Beijing (CN); Yue Tong, Beijing (CN); Yapeng Li, Beijing (CN); Jingjing Zhang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 0 days.

(21) Appl. No.: 18/027,108

(22) PCT Filed: Jan. 10, 2022

(86) PCT No.: PCT/CN2022/070938
§ 371 (c)(1),
(2) Date: Mar. 19, 2023

(87) PCT Pub. No.: WO2023/130431
PCT Pub. Date: Jul. 13, 2023

(65) Prior Publication Data
US 2024/0385457 A1 Nov. 21, 2024

(51) Int. Cl.
*G02B 27/01* (2006.01)
(52) U.S. Cl.
CPC ..... *G02B 27/0179* (2013.01); *G02B 27/0172* (2013.01); *G02B 2027/0187* (2013.01)

(58) Field of Classification Search
None
See application file for complete search history.

(56) References Cited

U.S. PATENT DOCUMENTS

| 2003/0058190 A1 | 3/2003 | Lewis et al. |
| 2016/0353094 A1 | 12/2016 | Rougeaux |

(Continued)

FOREIGN PATENT DOCUMENTS

| CN | 109715047 A | 5/2019 |
| CN | 109891296 A | 6/2019 |

(Continued)

*Primary Examiner* — Ryan Crockett
(74) *Attorney, Agent, or Firm* — WHDA, LLP

(57) ABSTRACT

An eye movement tracking device includes: a light source located at the light-emitting side of the display module and configured for providing a first light ray for irradiating an eye; a plurality of photoelectric sensing elements arranged in a non-display region of the display module and configured for receiving a second light ray to determine a position of a pupil of the eye; an optical structure located between the optical lens and the display module, including a plurality of optical transparent areas in one-to-one correspondence to the plurality of photoelectric sensing elements, each of the optical transparent areas being configured for transmitting the second light ray to a corresponding photoelectric sensing element; the second light ray being a light ray which passes through a center point of the optical lens after the first light ray is reflected back by the eye. An eye movement tracking method is also disclosed.

14 Claims, 5 Drawing Sheets

(56) References Cited

U.S. PATENT DOCUMENTS

| | | | |
|---|---|---|---|
| 2017/0262054 A1 | 9/2017 | Anman et al. | |
| 2018/0068449 A1* | 3/2018 | Malaika | G06V 40/19 |
| 2018/0114298 A1 | 4/2018 | Malaika et al. | |
| 2021/0063737 A1 | 3/2021 | Ling et al. | |
| 2022/0366819 A1 | 11/2022 | Gao et al. | |
| 2024/0004465 A1* | 1/2024 | Yamada | H04N 23/11 |
| 2024/0385443 A1* | 11/2024 | Hoenig | G02B 27/017 |
| 2025/0022414 A1* | 1/2025 | Cho | G09G 3/002 |

FOREIGN PATENT DOCUMENTS

| | | |
|---|---|---|
| CN | 110139091 A | 8/2019 |
| CN | 110208947 A | 9/2019 |
| CN | 110488494 A | 11/2019 |
| CN | 111766716 A | 10/2020 |
| CN | 113759556 A | 12/2021 |

\* cited by examiner

EYE MOVEMENT TRACKING DEVICE AND EYE MOVEMENT TRACKING METHOD

CROSS-REFERENCE TO RELATED APPLICATIONS

The present application is the U.S. national phase of PCT Application No. PCT/CN2022/070938 filed on Jan. 10, 2022, the disclosure of which is hereby incorporated by reference in its entirety.

TECHNICAL FIELD

The present disclosure relates to the technical field of display manufactures, and in particular, to an eye movement tracking device and an eye movement tracking method.

BACKGROUND

In a VR (virtual display) module structure, a VR lens group is disposed between an eye and a display screen. A diffuse light reflected back by the eyeball will be refracted after passing through the lens group, the refracted light then reaches a sensor (Sensor) through an optical aperture. The sensor receives the light carrying a signal reflected back by the eye, and a gazing position of the eye according to a magnitude of the signal is determined. In the VR lens group, the quantity of the lens cannot be large, due to the material and curved surface of the lens, and for the purpose of improving the overall aesthetics and reducing the product thickness. As a result, a lens distortion may exist when performing the eye tracking (eye movement tracking), resulting in an error in the magnitude of the signal received by the sensor.

SUMMARY

For addressing the above issue, in the present disclosure, an eye movement tracking device and an eye movement tracking method are provided, thereby addressing the issue of an error eye movement tracking caused by the optical distortion of the lens.

To achieve this, embodiments of the present disclosure provide the following technical solutions. An eye movement tracking device, applied to a near-eye display system, the near-eye display system including a display module and an optical lens located at a light-emitting side of the display module. The eye movement tracking device includes:
- a light source, located at the light-emitting side of the display module, the light source being configured for providing a first light ray which is emitted to an eye;
- a plurality of photoelectric sensing elements, arranged in a non-display region of the display module, the plurality of photoelectric sensing elements being configured for receiving a second light ray to determine a position of a pupil of the eye; and
- an optical structure, located between the optical lens and the display module, the optical structure comprising a plurality of optical transparent areas which is in one-to-one correspondence to the plurality of photoelectric sensing elements, each of the plurality of optical transparent areas being configured for transmitting the second light ray to a corresponding photoelectric sensing element of the plurality of photoelectric sensing elements;

the second light ray is a light ray which passes through a center point of the optical lens after the first light ray is reflected back by the eye.

Optionally, a center point of the eye, the center point of the optical lens and a center point of the display module are in a first straight line, and a position where one of the plurality of photoelectric sensing elements is located and a corresponding position in the pupil of the eye are located at two opposite sides of the first straight line.

Optionally, the non-display region comprises a first region extending in a first direction, and a first plurality of photoelectric sensing elements in the plurality of photoelectric sensing elements is distributed at intervals in the first region in the first direction.

The optical structure comprises a first portion extending in the first direction, and a first plurality of optical transparent areas in the plurality of optical transparent areas is distributed at intervals in the first portion in the first direction.

A center point of the first portion and a center point of the first region are in a second straight line, and a center point of each of the first plurality of optical transparent areas in the first portion is located at a side of a center point of a corresponding photoelectric sensing element facing the second straight line.

Optionally, in the first direction, the first region is divided into a plurality of first sub-regions, each of the plurality of first sub-regions is provided with one photoelectric sensing element, and areas of the plurality of first sub-regions successively increase from middle to two ends.

In the first direction, the first portion is divided into a plurality of first sub-portions, each of the plurality of first sub-portions is provided with one optical transparent area, and areas of the plurality of first sub-portions successively increase from middle to two ends.

Optionally, the non-display region further comprises a second region extending in a second direction, and a second plurality of photoelectric sensing elements in the plurality of photoelectric sensing elements is distributed at intervals in the second region in the second direction.

The optical structure comprises a second portion extending in the second direction, and a second plurality of optical transparent areas in the plurality of optical transparent areas is distributed at intervals in the second portion in the second direction.

A center point of the second portion and a center point of the second region are in a third straight line, and a center point of each of the second plurality of optical transparent areas in the second portion is located at a side of a center point of a corresponding photoelectric sensing element facing the third straight line.

The first direction intersects with the second direction.

Optionally, in the second direction, the second region is divided into a plurality of second sub-regions, each of the plurality of second sub-regions is provided with one photoelectric sensing element, and areas of the plurality of second sub-regions successively increase from middle to two ends.

In the second direction, the second portion is divided into a plurality of second sub-portions, each of the plurality of second sub-portions is provided with one optical transparent area, and areas of the plurality of second sub-portions successively increase from middle to two ends.

Optionally, a center point of the photoelectric sensing element is located at a side of a center point of a corresponding optical transparent area facing away from the first straight line.

Optionally, the optical structure has an annular shape, and an orthographic projection of the optical structure onto the display module is located in the non-display region of the display module.

Optionally, the optical structure is integrated with the display module, the display module comprises a frame, and the plurality of optical transparent areas each corresponds to a through hole provided in the frame.

Optionally, a light-emitting surface of the display module is provided with a light-shielding layer having a hollowed pattern for forming the plurality of optical transparent areas.

Optionally, the non-display region includes a first region extending in a first direction and a second region extending in a second direction, the first direction intersects with the second direction, and the plurality of photoelectric sensing elements includes a plurality of first photoelectric components distributed in the first region and a plurality of second photoelectric components distributed in the second region.

In the first direction, the first region is divided into a plurality of first sub-regions, each of the first sub-regions is provided with one first photoelectric sensing element, and areas of the plurality of first sub-regions successively increase from middle to two ends.

In the second direction, the second region is divided into a plurality of second sub-regions, each of the second sub-regions is provided with one second photoelectric sensing element, and areas of the plurality of second sub-regions successively increase from middle to two ends.

Optionally, the frame includes a first frame corresponding to the first region, and a second frame corresponding to the second region.

In the first direction, the first frame is divided into a plurality of first sub-frames, each of the first sub-frames is provided with one optical transparent area, and areas of the plurality of first sub-frames successively increase from middle to two ends.

In the second direction, the second frame is divided into a plurality of second sub-frames, each of the second sub-frames is provided with one optical transparent area, and areas of the plurality of second sub-frames successively increase from middle to two ends.

Optionally, the second light ray passing through the optical transparent area satisfies a Lambertian distribution, and a distribution width for the second light ray is less than a distance between two adjacent ones of the plurality of photoelectric sensing elements.

Optionally, the light source comprises a lamp ring surrounding a periphery of the optical lens, and a plurality of infrared light-emitting diode (LED) lamp beads are arranged at the lamp ring.

Optionally, a distance between the optical structure and the photoelectric sensing element ranges from 500 μm to 700 μm.

In another embodiment of the present disclosure, an eye movement tracking method, applied to the eye movement tracking device described above is provided, the method including:

receiving a light which is emitted by a plurality of light sources and then reflected back by a human eye;
converting the received light into an electrical signal; and
determining, based on a signal value of the electrical signal and a position of at least one photoelectric sensing element, a position of a pupil of the eye.

According to the present disclosure, various advantages can be achieved. The light ray passing through the optical transparent area is the light ray that passes through the center of the optical lens, namely, the light ray received by the photoelectric sensing element is a collimated light ray that passes through the optical center of the optical lens. As compared with receiving light through the edge of the lens, the configuration of the present disclosure can reduce or even eliminate an optical distortion of the lens, thereby improving the accuracy of the eye movement tracking.

DETAILED DESCRIPTION

To make objects, technical solutions and advantages of embodiments of the present disclosure more clearly, a clear description of the embodiments of the present disclosure will be given in conjunction with the appended drawings hereinafter. It is to be understood that the described embodiments are merely some, but not all, of the embodiments of the present disclosure. Based on the described embodiments of the present disclosure, all other embodiments obtained by one of ordinary skill in the art fall within the scope of the present disclosure.

In description of the present disclosure, it should be noted that orientations or positional relationships indicated by the terms "center", "upper", "lower", "left", "right", "vertical", "horizontal", "inner", "outer", and the like are based on the orientations or positional relationships shown in the figures. This is merely to facilitate description of the present disclosure and simplify the description, and do not indicate or imply that the referenced devices or elements must have the particular orientation, be constructed and operated in the particular orientation, and thus should not be interpreted as a limitation on the present disclosure. Furthermore, the terms "first", "second", and "third" are used for descriptive purposes only and are not to be interpreted as indicating or implying relative importance.

Figures 1, 2, 3:
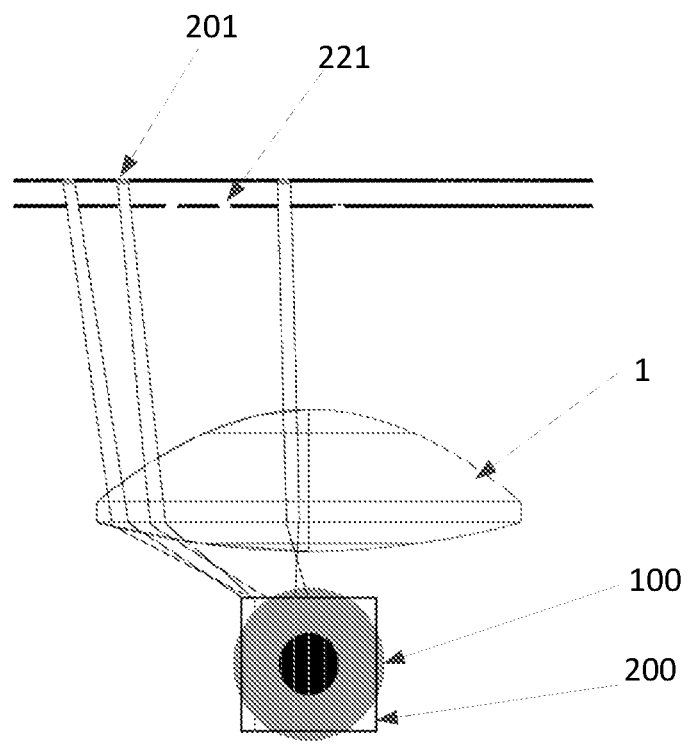
FIG. 1 is a schematic diagram of a signal for a straight line passing through a center of a lens.
FIG. 2 shows a schematic diagram of a distorted signal passing through an edge of a lens.
FIG. 3 is a schematic diagram showing an optical path for eye movement tracking in the related art.

Pupil-positioning technique: a pupil area of an iris of an eye is black. This pupil area has stronger ability to absorb light, resulting in less reflected light in the pu53pil area and more reflected light in other areas. FIG. 1 shows a diagram of a signal for a straight line at the center of the lens, which may become a curved line (barrel distortion) if it pass through the edge of the lens, with reference to FIG. 2. The optical distortion may not only reduce the imaging quality, but also cause a small difference in the magnitudes of signals received by the sensors, which is disadvantageous for realizing the function of eye tracking (eye movement tracking).

Figure 5:
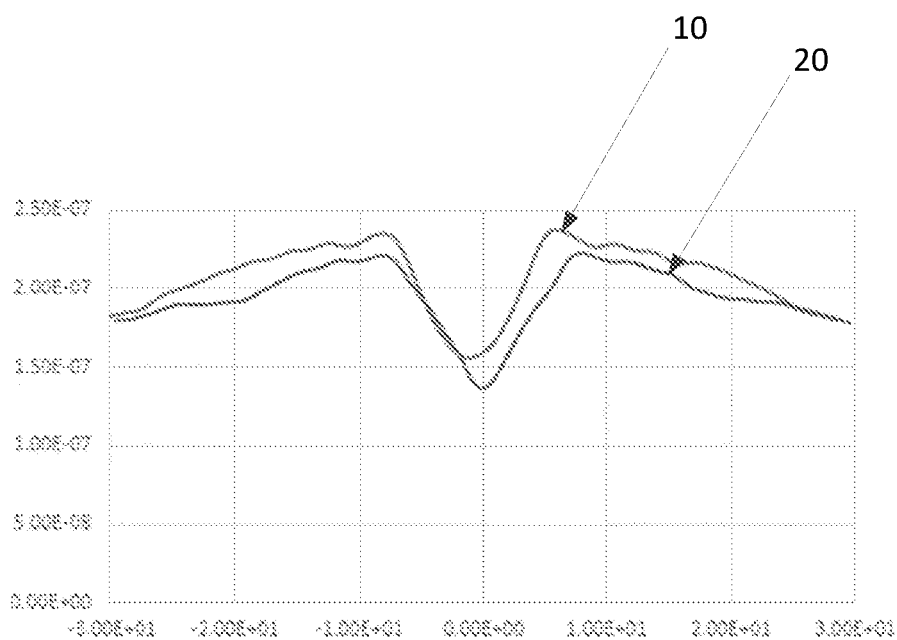
FIG. 5 is a schematic diagram of a magnitude of a signal received by a photoelectric sensing element.

FIG. 3 is a schematic diagram of an optical path for the eye movement tracking in the related art. In the optical path, a light ray is exited from an edge position of an optical lens 1, and then is received via a collimating structure. The signal magnitudes received by sensors of a display module 2 may be affected by the distortion at lens edge. FIG. 5 is a graph comparing the magnitudes of the signals received by the sensors before and after a rotation of the eyeball, wherein the horizontal axis in FIG. 5 denotes the position of the sensors, and the vertical axis denotes the magnitude of the signals received by the sensors. The first curve 20 is a curve of the signal magnitudes received by the sensors in the horizontal x-axis direction when the eye gazes at the center, and it can be seen that the signal magnitude received by the sensor located at the center position is the minimum. The second curve 10 is a curve of the signal magnitudes received by the sensors in x-axis direction when the eye moves to the left, and it can be seen that the position of the signal having the minimum magnitude changes with the rotation of the eyeball. In the recognition process of eye movement tracking, the distortion effect of the lens may cause a change of the highest point S2 and the lowest point S1 of each curve for the signal magnitude in FIG. 5, where $\Delta S=S2-S1$. In the process of eye movement recognition, a large $\Delta S$ is beneficial to the recognition of the pupil gazing position, and the distortion of the lens may result in a reduced difference in the signal magnitudes $\Delta S$.

Figure 7:
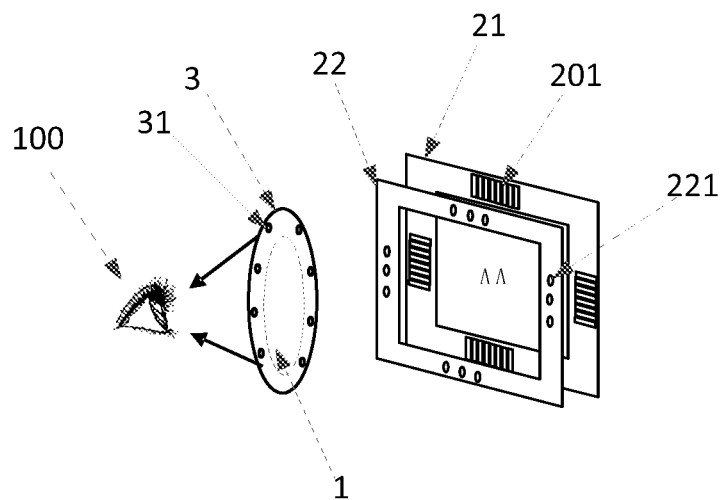
FIG. 7 is a schematic diagram showing a structure of an eye movement tracking device in an embodiment of the present disclosure.

With reference to FIG. 7, to address the above issue, embodiments of this disclosure provides an eye movement tracking device, applied to a near-eye display system, the near-eye display system includes a display module 21 and an optical lens 1 located at a light-emitting side of the display module 21. The eye movement tracking device includes the following elements:

a light source 3, located at the light-emitting side of the display module 21, the light source 3 is configured for providing a first light ray to be incident on an eye 100;

a plurality of photoelectric sensing elements 201, arranged in a non-display region of the display module 21, and configured for receiving a second light ray to determine a position of a pupil of the eye; and an optical structure 22, located between the optical lens 1 and the display module 21, the optical structure 22 includes a plurality of optical transparent areas 221 which is in one-to-one correspondence to the plurality of photoelectric sensing elements 201, each of the optical transparent areas 221 allows the second light ray passing through to reach a corresponding photoelectric sensing element 201;

the second light ray is such a light ray, which the first light ray is reflected back by the eye 100, and the reflected light ray passes through a center point of the optical lens 1 (the center point is located in the optical axis of the optical lens).

The optical transparent areas 221 correspond to the photoelectric sensing elements 201 on a one-to-one basis, namely, one of the optical transparent areas 221 is used for transmitting a second light ray to a corresponding one of the photoelectric sensing elements 201. Different ones of the photoelectric sensing elements 201 correspond to different regions of the eye 100, respectively, and therefore the position of the pupil of the eye may be determined based on position coordinates of the photoelectric sensing elements 201.

In addition, with the above-mentioned technical solution of the present embodiment, the light ray passing through the optical transparent area 221 is a light ray that passes through the center of the optical lens 1 (namely, the second light ray), and the light ray received by the photoelectric sensing element 201 is a collimated light ray that passes through optical center of the optical lens 1. With use of this structure, the optical distortion due to the lens can be reduced or even eliminated as compared with a solution in which the light passing through the edge of the lens is received, thereby improving the accuracy of the eye movement tracking.

Figure 4:
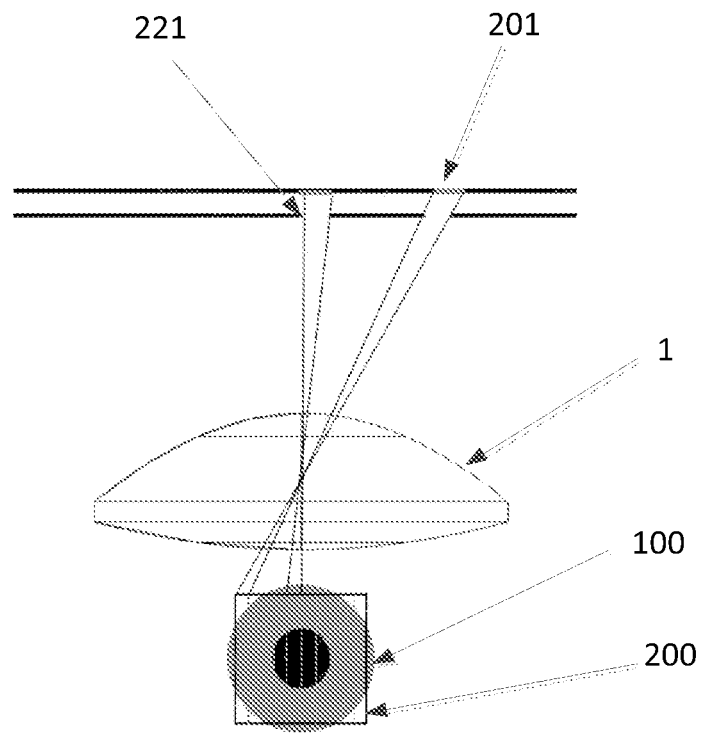
FIG. 4 is a schematic diagram showing an optical path for eye movement tracking in an embodiment of the present disclosure.

With reference to FIG. 4, in this embodiment, illustratively, a center point of the eye 100, the center point of the optical lens 1 and a center point of the display module 21 are in a first straight line, and a position where one of the photoelectric sensing elements 201 is located and a corresponding position in the pupil of the eye are located at two opposite sides of the first straight line.

It should be understood that the center point of the eye refers to the center point of the eyeball.

As shown in FIG. 4, what received by the photoelectric sensing element 201 is a signal in an opposite direction, namely, a photoelectric sensing element 201 on the rightmost side receives a component signal of the leftmost part of an eye box region 200 (an eye box is referred to as a field of view region of a screen where the eye can see in the VR environment) of an eye, that is, receives a light signal reflected back by the leftmost part of the eye. A photoelectric sensing element 201 on the lower side receives a component signal of the upper part of the eye box region 200 (namely, receiving a light signal reflected back by the upper part of the eye). In this structure, when the eye gazing direction moves to the left, the point denoting the signal having the minimum magnitude moves to the right, which is opposite to the movement of gazing direction. It should be noted that the eye gazing direction is determined by the position of the pupil, and the movement direction of the eye gazing point is the movement direction of the pupil.

Figure 6:
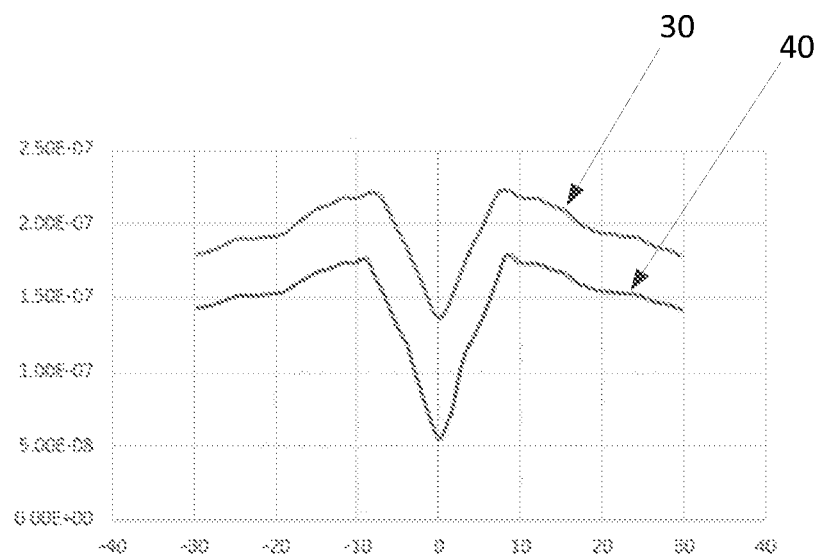
FIG. 6 is a schematic diagram comparing a magnitude of a signal received by a photoelectric sensing element of an eye movement tracking device in the related art with a magnitude of a signal received by a photoelectric sensing element of an eye movement tracking device in an embodiment of the present disclosure.

In FIG. 6, the third curve 30 is a curve for a signal magnitude of a conventional structure, where $\Delta S/S2=(S2-S1)/S2=0.34$, and the fourth curve 40 is a curve for a signal magnitude of an optimized structure, where $\Delta S/S2=(S2-S1)/S2=0.69$ (this data represents relative values, and the specific values may change when the structure and experimental conditions change), the change in the signal magnitude for the pupil gazing region becomes larger, and the distortion effect of the eye tracking in the VR structure is improved.

Figure 8:
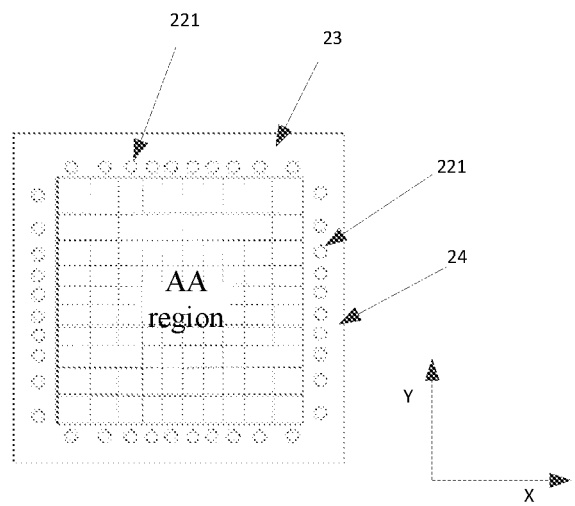
FIG. 8 is a schematic diagram showing a distribution of optical transparent areas.
Figure 9:
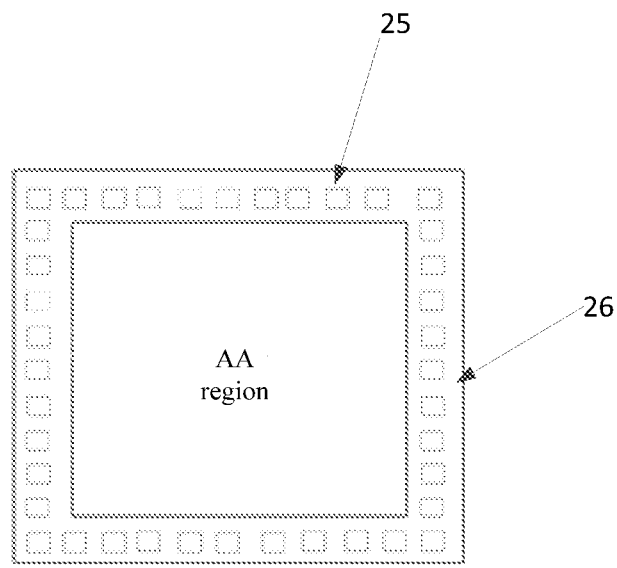
FIG. 9 is a schematic diagram showing a distribution of photoelectric sensing elements.

With reference to FIGS. 4, 8 and 9, illustratively, the non-display region includes a first region 25 extending in a first direction (e.g., the X direction in FIG. 8), and multiple photoelectric sensing elements 201 are distributed, at intervals along the first direction, in the first region 25.

The optical structure includes a first portion 23 extending in the first direction, and multiple optical transparent areas 221 are distributed, at intervals along the first direction, in the first portion 23.

A center point of the first portion 23 and a center point of the first region 25 are in a second straight line, and a center point of each of the multiple optical transparent areas 221 in the first portion 23 is located at a side of a center point of a corresponding photoelectric sensing element 201 facing the second straight line, see FIG. 4.

FIG. 4 shows a photoelectric sensing element 201 arranged on the rightmost in the first direction, and an optical transparent area 221 corresponding to this photoelectric sensing element. The photoelectric sensing element 201 receives a light ray which is reflected back by the leftmost part of the eye (corresponding to the leftmost partition of the eye box region 200) and then passing through the optical lens 1. The photoelectric sensing element 201 is located at the right side of the optical transparent area 221 corresponding thereto, so that the second light ray passing through the center of the optical lens 1 can be received by the photoelectric sensing element 201.

Illustratively, and for the same principle as above, the non-display region further includes a second region 26 extending in a second direction (e.g., the Y-direction in FIG. 8), and multiple photoelectric sensing elements 201 are distributed, at intervals along the second direction, in the second region 26.

The optical structure includes a second portion 24 extending in the second direction, and multiple optical transparent areas 221 are distributed, at intervals along the second direction, in the second portion 24.

A center point of the second portion 24 and a center point of the second region 26 are in a third straight line, and a center point of each of the multiple optical transparent areas 221 in the second portion 24 is located at a side of a center point of a corresponding photoelectric sensing element 201 facing the third straight line.

The first direction intersects with the second direction.

With reference to FIGS. 8 and 9, the non-display region of the display module is annular, four edges of the display module are all provided with photoelectric sensing elements 201, and corresponding four edges of the optical structure are also all provided with optical transparent areas 221.

The display module 21 is generally rectangular, and the first direction and the second direction are arranged perpendicular to each other. A coordinate system is established with the display module 21 as a reference, such that position coordinates of each of the photoelectric sensing elements 201 may be obtained, and the position of the pupil of the eye can be determined according to the signal magnitude of light absorbed by each of the photoelectric sensing elements 201.

Illustratively, the center point of the photoelectric sensing element 201 is located at a side of the center point of the corresponding optical transparent area 221 facing away from the first straight line.

In order not to affect the normal display of the display module 21, the photoelectric sensing elements 201 are arranged in the non-display region of the display module 21, the center point of the eye, the center point of the optical lens 1 and the center point of the display module are in the first straight line, and the first straight line is parallel to the light output direction of the display module, and the center point of the photoelectric sensing element 201 is located at a side of the center point of the corresponding optical transparent area 221 facing away from the first straight line, so as to facilitate the reception of light by the photoelectric sensing element 201.

Illustratively, in the first direction, the first region 25 is divided into a plurality of first sub-regions, each of the plurality of first sub-regions is provided with one photoelectric sensing element 201, and areas of the first sub-regions successively increase from middle to two ends.

In the first direction, the first portion 23 is divided into a plurality of first sub-portions, each of the first sub-portions is provided with one optical transparent area 221, and areas of the first sub-portions successively increase from middle to two ends.

In the second direction, the second region 26 is divided into a plurality of second sub-regions, each of the second sub-regions is provided with one photoelectric sensing element 201, and areas of the second sub-regions successively increase from middle to two ends.

Illustratively, in the second direction, the second portion 24 is divided into a plurality of second sub-portions, each of the second sub-portions is provided with one optical transparent area 221, and areas of the second sub-portions successively increase from middle to two ends.

Since the fluctuation in the signal magnitudes received by the photoelectric sensing elements 201 located at the two ends in the first direction are great, and there may be a greater fluctuation in the signal magnitude received by the photoelectric sensing elements 201 which is farther away from the center point. This may affect the determination of the position of the pupil. Therefore, in the present embodiment, the first region 25 is divided into sub-regions, and the areas of the first sub-regions successively increase from middle to two ends, so as to address the following issue: the accuracy of the determination of the position of the pupil may be affected by the large fluctuation in the signal magnitudes received by the first photoelectric sensing elements 2011 located at the two ends.

Similarly, in the second direction, the fluctuation in the signal magnitudes received by the photoelectric sensing elements 201 located at the two ends are great, and there may be a greater fluctuation in the signal magnitude received by the photoelectric sensing elements 201 which is farther away from the center point. This may affect the determination of the pupil position. Therefore, in the present embodiment, the second region 26 is divided into sub-regions, and the areas of the second sub-regions successively increase from middle to the two ends, so as to address the following issue: the accuracy of the determination of the position of the pupil may be affected by the large fluctuation in the signal magnitudes received by the first photoelectric sensing elements 2012 located at the two ends.

The display module in the present embodiment may comprise an LCD display module. In the VR display environment, the user needs to watch the display screen through a square eye box region 200 in front of the eye, and the eye movement tracking can be realized by detecting the position of the eye on the eye box region 200 (see FIGS. 3 and 4). The eye box is referred to as a field of view region where the eye can see the screen under the VR environment, with a size of 8*8 mm, and the eye box region is subjected to a 10*10 partitioning. When the eye rotates, the pupil may be in different partitions, the photoelectric sensing elements corresponding to different partitions will receive different magnitudes of signals. The position of the pupil can be determined accordingly, and, in turn, the position where the eyeball is gazing at can be determined. The optical transparent areas 221 and the photoelectric sensing elements 201 are arranged in different partitions corresponding to the partitions of the eye box. With reference to FIGS. 8 and 9, the 10*10 partitioning adopts a unevenly distribution, namely, the partitioning is performed in a manner in which the partitions gradually increases from the center to the two ends in the first direction (see the X direction in FIG. 8), and the partitions gradually increases from the center to the two ends in the second direction (see the Y direction in FIG. 9).

This is because: 1, in the near-eye eye-tracking VR module, the signal magnitude received by the photoelectric sensing element is at a low level, and the signal magnitude of the light source exited from the eye box has a great influence on the reception of the photoelectric sensing element, so that in case of no eye, the signal magnitudes received by different photoelectric sensing elements should be ensured to be equal; 2, as compared with the photoelectric sensing element at middle position, the photoelectric sensing element at the end position corresponds to a light ray having a longer optical path, and thus, a higher loss, a larger partition can compensate for such a loss; and 3, reference of the signal magnitudes: the difference in the signal magnitudes received by any two photoelectric sensing elements should be ensured to be less than 10%, so as to avoid the influence of an excessive fluctuation on the determination of pupil position.

In a specific implementation of the present embodiment, the position coordinates of the optical transparent areas 221 arranged in the first direction are shown in Table 1, and the position coordinates of the photoelectric sensing elements 201 arranged in the first direction corresponding to the optical transparent areas in Table 1 are shown in Table 2.

TABLE 1

| x | y | z |
|---|---|---|
| −27.6287 | 30.0761 | 0 |
| −21.489 | 30.0761 | 0 |
| −15.3493 | 30.0761 | 0 |
| −9.2096 | 30.0761 | 0 |
| −3.0699 | 30.0761 | 0 |
| 3.0699 | 30.0761 | 0 |
| 9.2096 | 30.0761 | 0 |
| 15.3493 | 30.0761 | 0 |
| 21.489 | 30.0761 | 0 |
| 27.6287 | 30.0761 | 0 |

TABLE 2

| x | y | z |
|---|---|---|
| −27.9 | 31.025 | −0.5 |
| −21.7 | 31.025 | −0.5 |
| −15.5 | 31.025 | −0.5 |
| −9.3 | 31.025 | −0.5 |
| −3.1 | 31.025 | −0.5 |
| 3.1 | 31.025 | −0.5 |
| 9.3 | 31.025 | −0.5 |
| 15.5 | 31.025 | −0.5 |
| 21.7 | 31.025 | −0.5 |
| 27.9 | 31.025 | −0.5 |

As shown in FIGS. 7 and 8, illustratively, the optical structure 22 has an annular shape, and an orthographic projection of the optical structure onto the display module is located in the non-display region of the display module.

In a case that the orthographic projection of the optical structure 22 onto the display module is located in the non-display region of the display module, the normal display of the display module may not be influenced.

Illustratively, the optical structure 22 is integrated with the display module, the display module includes a frame, and through holes are provided in the frame to form the optical transparent areas 221.

Figure 12:
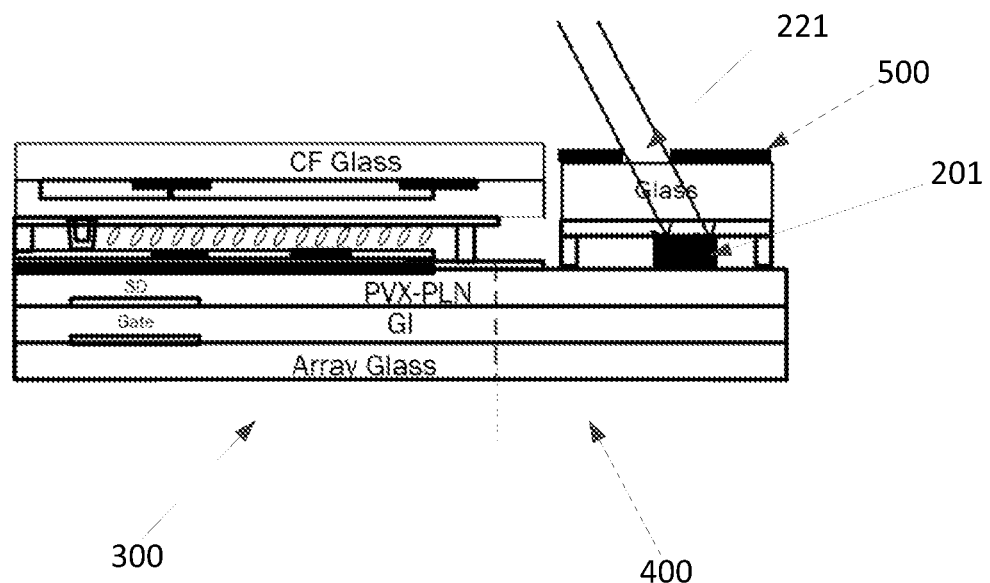
FIG. 12 is a schematic diagram showing a structure of a display module in an embodiment of the present disclosure.

As shown in FIGS. 7 and 12, illustratively, the display module 21 includes a display region 300 and a non-display region 400. A light-shielding layer 500 having a hollowed pattern is arranged located at a light-emitting surface of the display module 21 to form the optical transparent areas 221, the light-shielding layer 500 is located in the non-display region 400, and the hollowed pattern in the light-shielding layer 500 corresponds to the optical transparent areas 221.

With the above-mentioned technical solution, the structural arrangement can be simplified.

Illustratively, the second light ray passing through the optical transparent area 221 satisfies a Lambertian distribution, and the distribution width of the second light ray is less than a distance between two adjacent photoelectric sensing elements.

Figure 10:
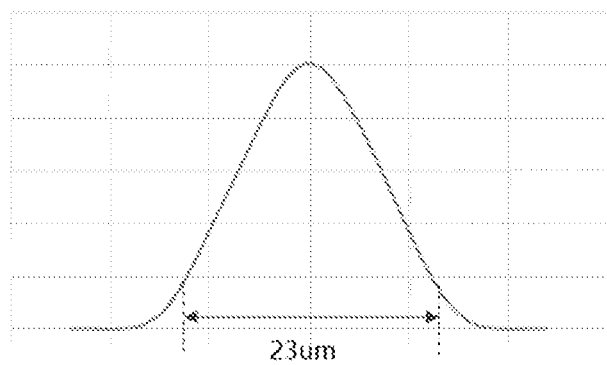
FIG. 10 is a schematic diagram showing a light distribution of the light passing through the optical transparent areas.

An example distribution of the second light ray after passing through one of the optical transparent areas is shown in FIG. 10. In the case that the distribution width for the second light ray is less than the distance between two adjacent photoelectric sensing elements, a crosstalk between light rays transmitted through adjacent optical transparent areas can be avoided.

For example, the display module is a 3.5 inch square screen (62.856 mm*62.856 mm), and the partitioning is 10*10, that is to say, 10 holes are provided at the edge (the edge at each side) of the screen of 6.2 cm size, to form 10 optical transparent areas 221, the optical transparent areas 221 each is a circular hole with a diameter of 10 μm, the irradiance of the light ray after passing through the optical transparent area 221 meets the Lambertian distribution, and the spectrum curve is shown in FIG. 10, in which the width of the spectrum curve is 23 μm (a width in the spectrum occupied by 90% of the energy after passing through the optical transparent area 221). The minimum interval between two adjacent optical transparent areas 221 may be, for example, 200 μm, to ensure no crosstalk between the adjacent optical transparent areas 221.

As shown in FIG. 7, illustratively, the light source 3 includes a lamp ring surrounding a periphery of the optical lens 1, and a plurality of infrared light-emitting diode (LED) lamp beads 31 are arranged on the lamp ring.

Figure 11:
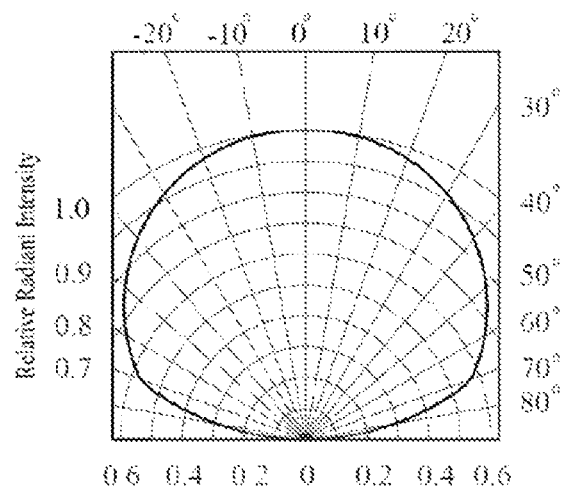
FIG. 11 is a schematic diagram showing a light-emitting angle of LED lamp beads.

In this embodiment, a light source of lamp ring has 8 infrared LEDs, the diameter of the lamp ring is 53.3 mm, the size of the LED lamp bead is 0.8 mm, the luminous power of a single light source is 10.53 mw, and a light-emitting angle is shown in FIG. 11. Light sources with other incident angles and intensities may also be used, the present disclosure is not limited thereto.

The light source 3 may also be a laser light source or the like, and the present disclosure is not limited thereto.

Illustratively, the distance between the optical structure 22 and the plurality of photoelectric sensing elements 201 may be in a range from 500 to 700 μm.

In the present embodiment, the optical lens 1 is a group of single lenses, the material is polymethyl methacrylate (PMMA), also known as Alec glass or plexiglass, with a refractive index n=1.49; the distance d1 from the eye to a first face of the lens (the face facing the eye) is 14 mm, the thickness d2 of the lens is 14 mm, and the distance d3 from a second face of the optical lens (the second face is opposite to the first face) to the display module is 33.7 mm. In this embodiment, the optical lens may be an aspherical lens, and the radius of curvature of the first face R1=−75.072 and the radius of curvature of the second face R2=22.861.

The following table shows the structural parameters of the eye movement tracking device in an example where the eye is of Asian race type, the pupil is black, and the iris is brownish-brown. The eyeballs of European and American are lighter in color and have poor infrared diffuse reflection, so this example does not take it into consideration. Diffuse reflectance of the eye for infrared light: the pupil 3-5%, the iris 10-20%, and the sclera 70-80%.

| Eyes (Asian) | Sclera (sclera) | Oval-like, about 30 mm in horizontal direction, about20 mm in longitudinal direction |
|---|---|---|
| | Iris (iris) | Round, about10 mm |
| | Pupil (pupil) | Round, under indoor environment, EPD about 4 mm |
| | IPD (interpupillary distance of an adult) | 64-68 mm |
| Optical lens | EFL (effective focal length) | 40 mm |
| | Eyerelief (eyerelief) | 14 mm |
| | Thickness | 14 mm |
| | Diameter | 40 mm |
| | Eye Box (range of eye movement) | 8 mm*8 mm |
| | File of view (for single eye) | Vr-Horizontal gazing FOV 90 degrees |
| | Eye - display | 61.7 mm |
| | BFL(Rear Face of the Vr Lens - display) | 33.7 mm |
| Display module | Size | LCD, 3.5 inch, square uncovered |
| | AA size | 62.856 mm*62.856 mm |
| | Resolution | 4320*4320 |
| | Luminance | 150 nit |
| | FPS, PPI | 90 Hz, 1746 ppi |
| | Contrast | >100000:1 |

An embodiment of the present disclosure further provides an eye movement tracking method, applied to the eye movement tracking device as described above, the method includes:
receiving a light which is emitted by a plurality of light sources and then reflected back by an eye;
converting the received light into an electrical signal; and
determining, based on a signal value of the electrical signal and a position of at least one photoelectric sensing element, a position of a pupil of the eye.

It is to be understood that the above-described embodiments are merely exemplary embodiments for the purpose of illustrating the principles of the present disclosure, and the disclosure is not limited thereto. Various modifications and variations that can be made by those skilled in the art without departing from the spirit or principles of the disclosure fall within the protection scope of the disclosure.

What is claimed is:

1. An eye movement tracking device, applied to a near-eye display system, the near-eye display system comprising a display module and an optical lens located at a light-emitting side of the display module, wherein the eye movement tracking device comprises:
a light source, located at the light-emitting side of the display module, the light source being configured for providing a first light ray which is emitted to an eye;
a plurality of photoelectric sensing elements, arranged in a non-display region of the display module, the plurality of photoelectric sensing elements being configured for receiving a second light ray to determine a position of a pupil of the eye; and
an optical structure, located between the optical lens and the display module, the optical structure comprising a plurality of optical transparent areas which is in one-to-one correspondence to the plurality of photoelectric sensing elements, each of the plurality of optical transparent areas being configured for transmitting the second light ray to a corresponding photoelectric sensing element of the plurality of photoelectric sensing elements;
wherein the second light ray is a light ray which passes through a center point of the optical lens after the first light ray is reflected back by the eye.

2. The eye movement tracking device according to claim 1, wherein a center point of the eye, the center point of the optical lens and a center point of the display module are in a first straight line, and a position where one of the plurality of photoelectric sensing elements is located and a corresponding position in the pupil of the eye are located at two opposite sides of the first straight line.

3. The eye movement tracking device according to claim 2, wherein the non-display region comprises a first region extending in a first direction, and a first plurality of photoelectric sensing elements in the plurality of photoelectric sensing elements is distributed at intervals in the first region in the first direction;
the optical structure comprises a first portion extending in the first direction, and a first plurality of optical transparent areas in the plurality of optical transparent areas is distributed at intervals in the first portion in the first direction; and
a center point of the first portion and a center point of the first region are in a second straight line, and a center point of each of the first plurality of optical transparent areas in the first portion is located at a side of a center point of a corresponding photoelectric sensing element facing the second straight line.

4. The eye movement tracking device according to claim 3, wherein in the first direction, the first region is divided into a plurality of first sub-regions, each of the plurality of first sub-regions is provided with one photoelectric sensing element, and areas of the plurality of first sub-regions successively increase from middle to two ends; and
in the first direction, the first portion is divided into a plurality of first sub-portions, each of the plurality of first sub-portions is provided with one optical transparent area, and areas of the plurality of first sub-portions successively increase from middle to two ends.

5. The eye movement tracking device according to claim 3, wherein the non-display region further comprises a second region extending in a second direction, and a second plurality of photoelectric sensing elements in the plurality of photoelectric sensing elements is distributed at intervals in the second region in the second direction;
the optical structure comprises a second portion extending in the second direction, and a second plurality of optical transparent areas in the plurality of optical transparent areas is distributed at intervals in the second portion in the second direction;
a center point of the second portion and a center point of the second region are in a third straight line, and a center point of each of the second plurality of optical transparent areas in the second portion is located at a side of a center point of a corresponding photoelectric sensing element facing the third straight line; and
the first direction intersects with the second direction.

6. The eye movement tracking device according to claim 5, wherein in the second direction, the second region is divided into a plurality of second sub-regions, each of the plurality of second sub-regions is provided with one photoelectric sensing element, and areas of the plurality of second sub-regions successively increase from middle to two ends;
in the second direction, the second portion is divided into a plurality of second sub-portions, each of the plurality of second sub-portions is provided with one optical transparent area, and areas of the plurality of second sub-portions successively increase from middle to two ends.

7. The eye movement tracking device according to claim 2, wherein a center point of the photoelectric sensing element is located at a side of a center point of a corresponding optical transparent area facing away from the first straight line.

8. The eye movement tracking device according to claim 1, wherein the optical structure has an annular shape, and an orthographic projection of the optical structure onto the display module is located in the non-display region of the display module.

9. The eye movement tracking device according to claim 8, wherein the optical structure is integrated with the display module, the display module comprises a frame, and the plurality of optical transparent areas each corresponds to a through hole provided in the frame.

10. The eye movement tracking device according to claim 8, wherein a light-emitting surface of the display module is provided with a light-shielding layer having a hollowed pattern for forming the plurality of optical transparent areas.

11. The eye movement tracking device according to claim 1, wherein the second light ray passing through the optical transparent area satisfies a Lambertian distribution, and a distribution width for the second light ray is less than a distance between two adjacent ones of the plurality of photoelectric sensing elements.

12. The eye movement tracking device according to claim 1, wherein the light source comprises a lamp ring surrounding a periphery of the optical lens, and a plurality of infrared light-emitting diode (LED) lamp beads are arranged at the lamp ring.

13. The eye movement tracking device according to claim 1, wherein a distance between the optical structure and the photoelectric sensing element ranges from 500 μm to 700 μm.

14. An eye movement tracking method, performed by the eye movement tracking device according to claim 1, the method comprising:
- receiving a light which is emitted by a plurality of light sources and then reflected back by a human eye;
- converting the received light into an electrical signal; and
- determining, based on a signal value of the electrical signal and a position of at least one photoelectric sensing element, a position of a pupil of the eye.

* * * * *